Dec. 18, 1956 E. S. BOERNER Plant Pat. 1,541
ROSE PLANT
Filed Jan. 5, 1956
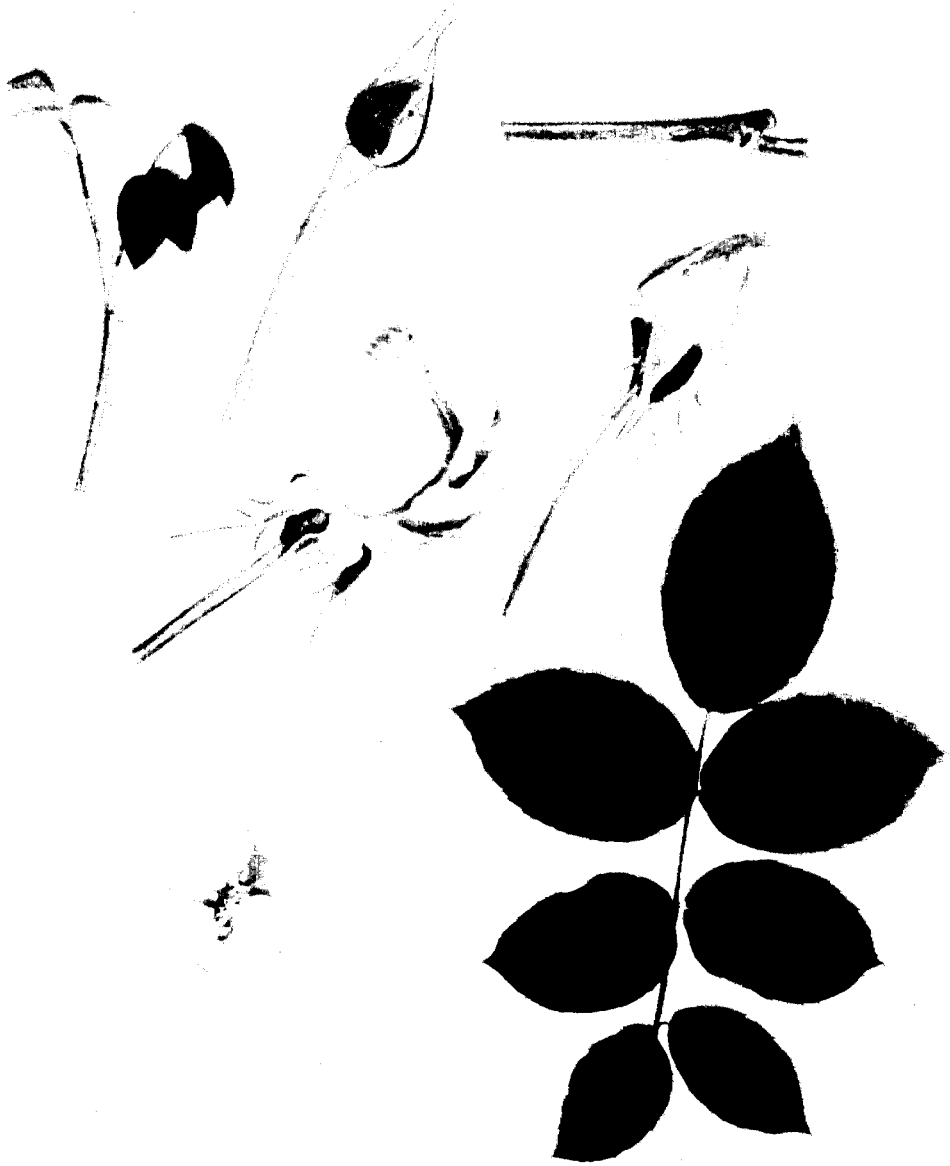
Inventor.
E. S. Boerner
By: Robb & Robb
Attorneys.

United States Patent Office

Plant Pat. 1,541
Patented Dec. 18, 1956

1,541

ROSE PLANT

Eugene S. Boerner, Newark, N. Y., assignor to Jackson & Perkins Company, Newark, N. Y., a corporation of New York Application January 5, 1956, Serial No. 557,620

1 Claim. (Cl. 47—61)

The present invention relates to a new and distinct variety of rose plant of the large-flowered polyantha class, which was originated by me by crossing the variety "Diamond Jubilee" (Plant Patent No. 824), with the variety "Fashion" (Plant Patent No. 789).

The primary objective in making this cross was to produce a new rose variety which combines the long-lasting keeping quality that is characteristic of the variety "Diamond Jubilee" with the typical characteristics of floribunda roses such as "Fashion." This objective was fully achieved, as evidenced by the following unique combination of features which are outstanding in my new variety:

(1) A very free flowering habit;

(2) An extremely rich fragrance;

(3) Long-lasting keeping quality of the flowers, both as cut flowers and on the bush in the garden; and (4) The distinctive Cameo Pink lightly overcast with Rose Pink general color tonality and the retention of the color for substantially the full life of the flowers.

Asexual reproduction of my new variety by budding, as performed at Newark, New York, and also at Pleasanton, California, shows that the foregoing characteristics and distinctions of my new variety come true to form and are established and transmitted through succeeding propagations.

The accompanying drawing shows typical specimens of the vegetative growth and flowers of my new variety in different stages of development and as depicted in color as nearly true as is reasonably possible to make the same in a color illustration of this character.

The following is a detailed description of my new variety, with color terminology in accordance with Robert Ridgway's Color Standards and Nomenclature:

Parentage: Seedling.
*Seed parent.*—"Diamond Jubilee."
*Pollen parent.*—"Fashion."
Classification:
*Botanic.*—Large-flowered polyantha.
*Commercial.*—Floribunda.

FLOWER (Observations made from specimens grown in a greenhouse at Newark, New York, about the middle of April and about mid-afternoon.)

Blooming habit: Recurrent—continuous.
Bud:
*Size.*—Medium.
*Form.*—Ovoid; is not affected by wet or hot weather.
*Color.*—When sepals first divide—Spinel Red, Plate 26. When petals begin to unfurl—Spectrum Red, Plate 1, lightly overcast with Spinel Red, Plate 26. When half-blown: Inside of petals—Hermonsa Pink, Plate 1, lightly overcast with Eosine Pink, Plate 1; reverse of petals—Begonia Rose, Plate 1, lightly overcast with Flesh Pink, Plate 13, in the center of the petal.

*Sepals.*—Branched; curl back when petals begin to unfurl. Color: Inside—Deep Turtle Green, Plate 32; outside—Rejane Green, Plate 33.
*Calyx.*—Color—Biscay Green, Plate 17. Shape—pear. Size—small. Aspect—smooth. Odor when rubbed—none.
*Peduncle.*—Length — medium. Aspect — smooth. Strength—erect; slender. Color—Light Cress Green, Plate 31.
*Opening.*—Opens up well; is not affected by adverse weather conditions.
Bloom:
*Size.*—Large. Average size when fully expanded—from 4 inches to 4½ inches.
*Borne.*—Several together and in irregular clusters.
*Stems.*—Medium length; normal strength.
*Form (when first open).*—High center. Permanence—retains its form to the end, but outer petals curl back.
*Petalage.*—Double (full but open center). Number of petals under normal conditions—from 65 to 70.
*Color.*—Center of flower—Deep Rose Pink, Plate 12, lightly overcast with Thulite Pink, Plate 26. Outer petals—Hermosa Pink, Plate 1. Base of petals (aiglet)—Strontian Yellow, Plate 16. Inside of petals—Cameo Pink, Plate 26, lightly overcast with Rose Pink, Plate 12. Reverse of petals—Hermosa Pink, Plate 1. General tonality from a distance—Cameo Pink, Plate 26, lightly overcast with Rose Pink, Plate 12.
*Discoloration.*—General tonality at end of first day—Cameo Pink, Plate 26, overcast with Rose Pink, Plate 12. Second day—Cameo Pink, Plate 26, lightly overcast with Rose Pink, Plate 12. Third day—Hermosa Pink, Plate 1, lightly overcast with Cameo Pink, Plate 26.
Petals:
*Texture.*—Leathery; is not affected by wet or hot weather.
*Appearance.*—Inside—satiny; outside—shiny.
*Form.*—Oval.
*Arrangement.* — Imbricated (regularly arranged shingle-like).
*Petaloids in center.*—Few; large.
*Persistence.*—Drop off cleanly.
*Fragrance.*—Very strong. Nature—Old Rose perfume (Centifolia).
*Lasting quality.*—On the plant—very long. As cut flower—very long.

GENITAL ORGANS

Stamens, anthers: Medium size; arranged regularly around styles; few. Color—Light Cadmium, Plate 4.
Stamens, filaments (threads): Medium length. Color—Marguerite Yellow, Plate 30.
Pollen: Color—Maize Yellow, Plate 4.
Styles: Columnar; uneven length; medium length; thin.
Stigmas: Color—Primrose Yellow, Plate 30.
Ovaries: All enclosed in calyx.
Hips: None.
Seeds: None.

PLANT

Form: Bush.
Growth: Vigorous; upright; bushy.
Foliage: Compound of 5 to 7 leaflets.
*Size.*—Medium.
*Quantity.*—Abundant.
*Color.*—New foliage: Upper side—Yellowish Oil Green, Plate 5, lightly overcast with Pompeian Red, Plate 13; under side—Acajou Red, Plate 13, with mid-rib of Yellowish Oil Green, Plate 5. Old foliage: Upper side—Dark Dull Yellow-Green, Plate 32; under side—Pois Green, Plate 41.

*Shape.*—Pointed.

*Texture.*—Upper side — glossy; smooth. Under side—smooth.

*Ribs and veins.*—Ordinary.

*Edge.*—Serrated (saw-toothed).

*Serration.*—Single; small.

*Leaf stem.*—Color—Light Hellebore Green, Plate 17. Under side—smooth.

*Stipules.*—Medium length; smooth.

Wood:

*New wood.*—Color—Oil Green, Plate 5. Bark—smooth.

*Old wood.*—Color—Spinach Green, Plate 5. Bark—smooth.

Thorns:

*Thorns.*—Quantity: On main stalks from base—ordinary; on laterals from stalk—ordinary. Form—Narrow base; medium length; hooked downward.

Color (when young)—Eugenia Red, Plate 13. Position—irregular.

*Prickles.*—Quantity: On main stalks—none; on laterals—none.

*Short needles.*—Quantity: On main stalks—none; on laterals—none.

I claim:

A new and distinct variety of rose plant of the large-flowered polyantha class, substantially as herein shown and described, characterized particularly as to novelty by its very free flowering habit, its extremely rich fragrance, the long-lasting keeping quality of its flowers both as cut flowers and on the bush, and the distinctive Cameo Pink lightly overcast with Rose Pink general color tonality of its flowers, said color being maintained without appreciable fading throughout substantially the entire life of the flowers.

No references cited.